US009612225B2

(12) United States Patent
Bai et al.

(10) Patent No.: US 9,612,225 B2
(45) Date of Patent: Apr. 4, 2017

(54) METHOD OF USING DUAL-PORT MEASUREMENT SYSTEM TO MEASURE ACOUSTIC IMPEDANCE

(71) Applicant: National Tsing Hua University, Hsinchu (TW)

(72) Inventors: Mingsian R. Bai, Hsinchu (TW); Yi-Yang Lo, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 232 days.

(21) Appl. No.: 14/521,755

(22) Filed: Oct. 23, 2014

(65) Prior Publication Data
US 2016/0077056 A1    Mar. 17, 2016

(30) Foreign Application Priority Data
Sep. 11, 2014 (TW) .............................. 103131298 A

(51) Int. Cl.
*G01N 29/028* (2006.01)
*G01N 29/09* (2006.01)
*G01N 29/24* (2006.01)
*G01N 29/44* (2006.01)

(52) U.S. Cl.
CPC ............. *G01N 29/09* (2013.01); *G01N 29/24* (2013.01); *G01N 29/4472* (2013.01); *G01N 2291/018* (2013.01)

(58) Field of Classification Search
CPC ................ G01N 29/09; G01N 29/024; G01N 2291/018; G01N 29/4472
USPC ........................................................... 73/589
See application file for complete search history.

(56) References Cited

U.S. PATENT DOCUMENTS

| 4,732,039 A * | 3/1988 | Syed ...................... G01H 15/00 |
| | | 73/588 |
| 2003/0221488 A1* | 12/2003 | Goldmeer .............. G01N 29/09 |
| | | 73/589 |

OTHER PUBLICATIONS

B.H. Song et al., "A transfer-matrix approach for estimating the characteristic.impedance and wave numbers of limp and rigid porous materials," J. Acoust. Soc. Am 107(3), Mar. 2000, pp. 1131-1152.

* cited by examiner

*Primary Examiner* — Helen Kwok
*Assistant Examiner* — Nashmiya Fayyaz
(74) *Attorney, Agent, or Firm* — Muncy, Geissler, Olds & Lowe, P.C.

(57) ABSTRACT

A method of using a dual-port measurement system to measure acoustic impedance is used to measure an acoustic impedance Z of a tested object. The tested object includes an input end and an output end opposite to the input end. The dual-port measurement system comprises a first impedance tube and a second impedance tube. The first impedance tube includes a first inlet where a plane wave of a sound source is input, and a first outlet connected with the input end. The second impedance tube includes a second inlet connected with the output end, and a second outlet where the plane wave is output. The method uses the dual-port measurement system and a two-boundary method to obtain the acoustic impedances Z, whereby the dual-port measurement system is conveniently applied to various fields, such as the design of earphones, muffler tubes, sound absorption materials, and artificial ears.

6 Claims, 10 Drawing Sheets

METHOD OF USING DUAL-PORT MEASUREMENT SYSTEM TO MEASURE ACOUSTIC IMPEDANCE

FIELD OF THE INVENTION

The present invention relates to a measurement method, particularly to a method of using a dual-port measurement system to measure acoustic impedance.

BACKGROUND OF THE INVENTION

While sound waves are conducted from one medium to another medium, the sound waves will be reflected, refracted or scattered in the interface between the two mediums, which depends on the difference of the acoustic impedances of the two mediums. Normally, the greater the difference of the acoustic impedances, the more intense the reflection. Some of the sound waves will be refracted in the medium behind the interface. If the dimension of the interface is smaller than the wavelength, scatter will occur. Therefore, the measurement of acoustic impedances is indispensable in designing and fabricating the products involving conduction or reception of sounds, such as earphones and artificial ears.

B. H. Song and J. S. Bolton proposed a paper "A transfer-matrix approach for estimating the characteristic impedance and wave numbers of limp and rigid porous materials" in J. Acoust. Soc. Am. 107, 1131-1152 (2000). The paper disclosed a measurement method of a dual-port measurement system. The dual-port measurement system comprises two impedance tubes, i.e. a first impedance tube and a second impedance tube. The terminal of the first impedance tube is the input end of the whole dual-port system; the start end of the second impedance tube is the output end of the whole dual-port system. The tested object is arranged between the input end and the output end. Each impedance tube has two microphones. The relationship between the sound pressure vectors measured by the microphone array and the transfer matrix are used to work out the incident waves and reflected waves of the first impedance tube and the second impedance tube. The incident waves and reflected waves are used to obtain the sound pressures and the volume velocities at the input end and the output end. Then, suppose the tested object satisfies symmetry and reciprocity, and use the relational equation of the output end and the input end to work out the transfer matrix and obtain the acoustic impedance of the tested object.

However, the abovementioned measurement method only applies to the test objects simultaneously satisfying symmetry and reciprocity and only adapts to a single algorithm. Thus, the conventional technology is only suitable to a single type of tested objects. Therefore, the application thereof is limited and inconvenient.

SUMMARY OF THE INVENTION

The primary objective of the present invention is to solve the problem that the conventional acoustic impedance measurement method is merely adapted to a single algorithm and only able to measure limited types of tested objects.

To achieve the abovementioned objective, the present invention proposes a method of using a dual-port measurement system to measure acoustic impedance, which is used to measure the acoustic impedance of a tested object. The tested object includes an input end and an output end opposite to the input end. The dual-port measurement system comprises a first impedance tube and a second impedance tube. The first impedance tube includes a first inlet where a plane wave of a sound source is input, and a first outlet connected with the input end of the tested object. The second impedance tube includes a second inlet connected with the output end of the tested object, and a second outlet where the plane wave is output. The method of the present invention comprises Step 1: arranging a plurality of microphones inside the first impedance tube and the second impedance tube respectively and lengthwise;

Step 2: expressing the sound pressures measured by the microphones inside the first impedance tube with $$p_M = Ae^{-jkx_M} + Be^{jkx_M}, \quad \text{Equation (1)}$$

and expressing the sound pressures measured by the microphones inside the second impedance tube with $$p_M = Ce^{-jkx_M} + De^{jkx_M}, \quad \text{Equation (2)}$$

wherein $p_M$ is the sound pressure measured by the Mth microphone, $x_M$ the position of the Mth microphone, A a first incident sound pressure, B a first reflected sound pressure, C a second incident sound pressure, D a second reflected sound pressure, k the wave number;

Step 3: using Equations (1) and (2) and the practical sound pressures measured by the microphones to work out A, B, C and D;

Step 4: expressing the input sound pressure of the input end with $$p_i(x_i) = Ae^{-jkx_i} + Be^{jkx_i}, \quad \text{Equation (3)}$$

expressing the input volume velocity with $$U_i(x_i) = \frac{S_{t1}}{\rho_0 c}(Ae^{-jkx_i} + Be^{jkx_i}), \quad \text{Equation (4)}$$

expressing the output sound pressure of the output end with $$p_o(x_o) = Ce^{-jkx_o} + De^{jkx_o}, \quad \text{Equation (5)}$$

and expressing the output volume velocity with $$U_o(x_o) = \frac{-S_{t2}}{\rho_0 c}(Ce^{-jkx_o} - De^{jkx_o}), \quad \text{Equation (6)}$$

wherein $\rho_0$ is the density of the air, $S_{t1}$ the cross-sectional area of the first impedance tube, $S_{t2}$ the cross-sectional area of the second impedance tube, $x_i$ the position of the input end, and $x_o$ the position of the output end;

Step 5: expressing the acoustic impedance with $$Z = \begin{bmatrix} z_{11} & z_{12} \\ z_{21} & z_{22} \end{bmatrix}, \quad \text{Equation (7)}$$

undertaking measurements at the second outlet in an opened condition and a closed condition, and using $$\begin{bmatrix} z_{11} & z_{12} \\ z_{21} & z_{22} \end{bmatrix} \begin{bmatrix} U_i \\ U_o \end{bmatrix} = \begin{bmatrix} p_i \\ p_o \end{bmatrix} \quad \text{Equation (8)}$$

to work out the acoustic impedance Z.

Thereby, the present invention uses the dual-port measurement system, which is adaptive to various types of tested objects, to obtain the acoustic impedances Z of the tested objects. The present invention is conveniently applied to various fields, such as the design of earphones, muffler tubes, sound absorption materials, and artificial ears.

DETAILED DESCRIPTION OF THE PREFERRED EMBODIMENTS

The technical contents of the present invention will be described in detail in cooperation with drawings below.

Figure 1A:
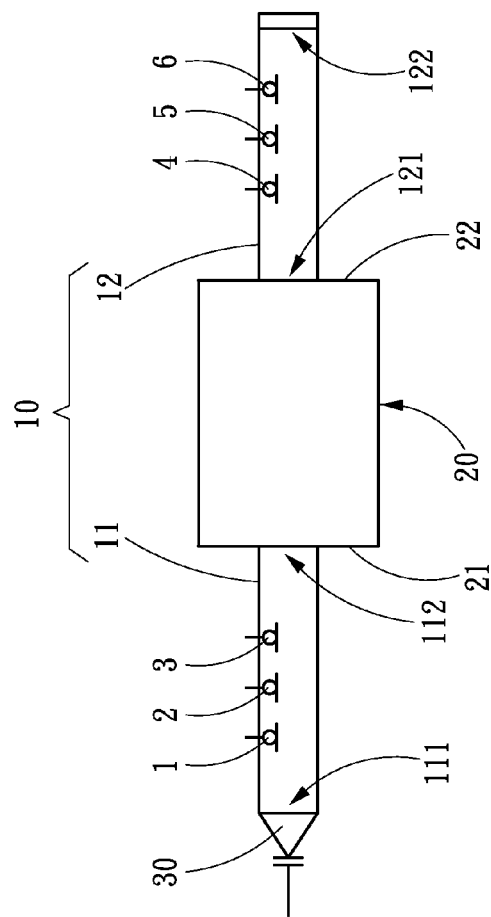
FIG. 1A is a diagram schematically showing a dual-port measurement system according to one embodiment of the present invention.
Figure 1B:
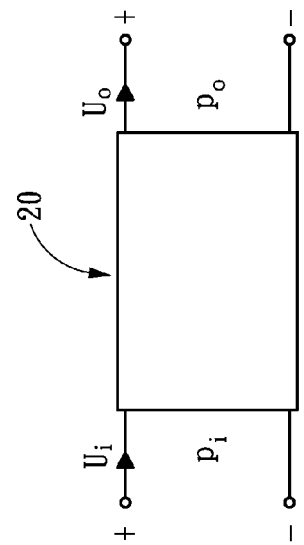
FIG. 1B is a diagram schematically showing the principle of a dual-port measurement according to one embodiment of the present invention.
Figure 2A:
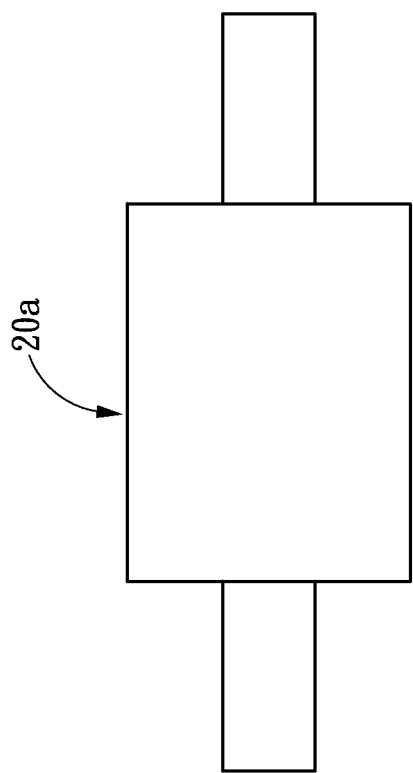
FIG. 2A is a diagram schematically showing a symmetric tested object according to one embodiment of the present invention.
Figure 2B:
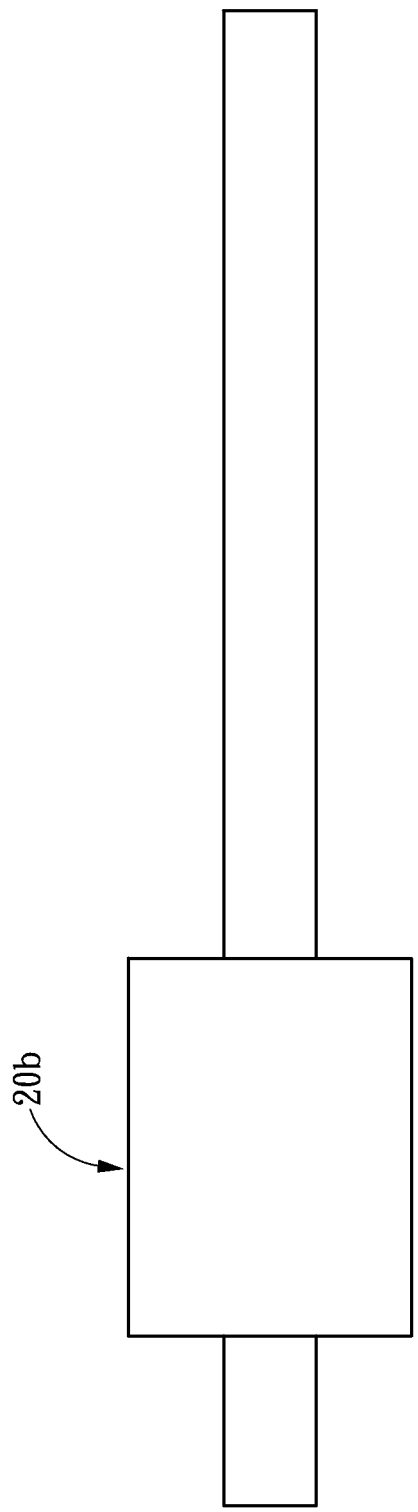
FIG. 2B is a diagram schematically showing an asymmetric tested object according to one embodiment of the present invention.
Figure 2C:
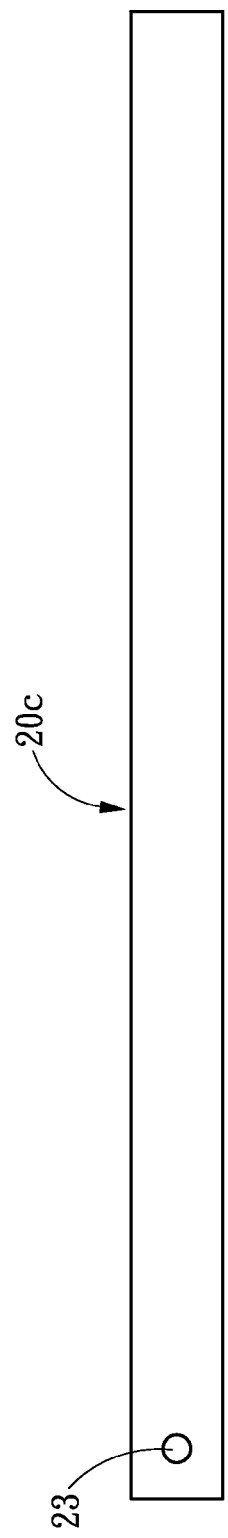
FIG. 2C is a diagram schematically showing an asymmetric tested object including a sound source according to one embodiment of the present invention.

Refer to FIG. 1A, FIG. 1B, and FIGS. 2A-2C. FIG. 1A is a diagram schematically showing a dual-port measurement system according to one embodiment of the present invention. FIG. 1B is a diagram schematically showing the principle of a dual-port measurement according to one embodiment of the present invention. FIGS. 2A-2C are diagrams schematically showing different tested objects measured by a dual-port measurement system according to one embodiment of the present invention. The present invention proposes a method of using a dual-port measurement system 10 to measure acoustic impedance, which is used to measure the acoustic impedance Z of a tested object 20. The tested object 20 may be a symmetric tested object 20a (as shown in FIG. 2A), an asymmetric tested object 20b (as shown in FIG. 2B), or an asymmetric tested 20c including a sound source 23 (as shown in FIG. 2C). The tested object 20 includes an input end 21 and an output end 22 opposite to the input end 21.

The dual-port measurement system 10 comprises a first impedance tube 11 and a second impedance tube 12. The first impedance tube 11 includes a first inlet 111 where a plane wave of a sound source 30 is input, and a first outlet 112 connected with the input end 21 of the tested object 20. The second impedance tube 12 includes a second inlet 121 connected with the output end 22 of the tested object 20, and a second outlet 122 where the plane wave is output. In the embodiment shown in FIG. 1A, the sound source 30 is a speaker. The speaker emits a sound wave having a cut-off frequency fc, and $$f_c = \frac{\pi c}{2\pi l},$$

wherein c is the sound velocity, and l the largest length of the cross-section of the first impedance tube 11, whereby the sound wave propagates inside the first impedance tube 11 in form of a plane wave.

The method of the present invention comprises Steps 1-5.

In Step 1, respectively lengthwise arrange a plurality of microphones 1-6 inside the first impedance tube 11 and the second impedance tube 12. In the embodiment shown in FIG. 1A, three microphones 1-3 are arranged inside the first impedance tube 11, and three microphones 4-6 are arranged inside the second impedance tube 12. However, the present invention does not limit the way of microphone arrangement.

In Step 2, express the sound pressures measured by the microphones 1-3 inside the first impedance tube 11 with $$p_M = Ae^{-jkx_M} + Be^{jkx_M}, \text{ and} \quad \text{Equation (1)}$$

express the sound pressures measured by the microphones 4-6 inside the second impedance tube 12 with $$p_M = Ce^{-jkx_M} + De^{jkx_M}, \quad \text{Equation (2)}$$

wherein $p_M$ is the sound pressure measured by the Mth microphone, $x_M$ the position of the Mth microphone, A a first incident sound pressure, B a first reflected sound pressure, C a second incident sound pressure, D a second reflected sound pressure, and k the wave number. For example, in FIG. 1A, let the microphone 1, which is near the first inlet 111 of the first impedance tube 11, be the first microphone 1, and let the position of the first microphone 1 be $x_1$; thus, the sound pressure $p_1$ measured by first microphone 1 is expressed by $$p_1 = Ae^{-jkx_1} + Be^{jkx_1}. \quad \text{Equation (1a)}$$

Similarly, the sound pressure $p_2$ measured by second microphone 2 is expressed by $$p_2 = Ae^{-jkx_2} + Be^{jkx_2}; \quad \text{Equation (1b)}$$

the sound pressure $p_3$ measured by third microphone 3 is expressed by $$p_3 = Ae^{-jkx_3} + Be^{jkx_3}. \quad \text{Equation (1c)}$$

Let the microphone 4, which is near the second inlet 121 of the second impedance tube 12, be the fourth microphone 4; thus, the sound pressure $p_4$ measured by the fourth microphone 4 is expressed by $$p_4 = Ce^{-jkx_4} + De^{jkx_4}. \quad \text{Equation (2a)}$$

Similarly, the sound pressure $p_5$ measured by the fifth microphone 5 is expressed by $$p_5 = Ce^{-jkx_5} + De^{jkx_5}; \quad \text{Equation (2b)}$$

the sound pressure $p_6$ measured by the sixth microphone 6 is expressed by $$p_6 = Ce^{-jkx_6} + De^{jkx_6}. \quad \text{Equation (2c)}$$

In Step 3, use Equations (1) and (2) and the practical sound pressures measured by the microphones 1-6 to work out A, B, C and D. In the embodiment shown in FIG. 1A, Equations (1a), (1b) and (1c) are rearranged to obtain $$\begin{bmatrix} p_1 \\ p_2 \\ p_3 \end{bmatrix} = \begin{bmatrix} e^{-jkx_1} & e^{jkx_1} \\ e^{-jkx_2} & e^{jkx_2} \\ e^{-jkx_3} & e^{jkx_3} \end{bmatrix} \begin{bmatrix} A \\ B \end{bmatrix} \quad \text{Equation (1d)}$$

The given values of $p_1$, $p_2$, $p_3$, $x_1$, $x_2$, and $x_3$ are used to solve Equation (1d) to obtain the values of A and B. Similarly, Equations (2a), (2b) and (2c) are rearranged to obtain $$\begin{bmatrix} p_4 \\ p_5 \\ p_6 \end{bmatrix} = \begin{bmatrix} e^{-jkx_4} & e^{jkx_4} \\ e^{-jkx_5} & e^{jkx_5} \\ e^{-jkx_6} & e^{jkx_6} \end{bmatrix} \begin{bmatrix} C \\ D \end{bmatrix} \quad \text{Equation (2d)}$$

The given values of $p_4$, $p_5$, $p_6$, $x_4$, $x_5$, and $x_6$ are used to solve Equation (2d) to obtain the values of C and D.

In Step 4, express the input sound pressure of the input end 21 with $$p_i(x_i) = Ae^{-jkx_i} + Be^{jkx_i}, \quad \text{Equation (3)}$$

express the input volume velocity with $$U_i(x_i) = \frac{S_{t1}}{\rho_0 c}(Ae^{-jkx_i} - Be^{jkx_i}), \quad \text{Equation (4)}$$

express the output sound pressure of the output end 22 with $$p_o(x_o) = Ce^{-jkx_o} + De^{jkx_o}, \text{ and} \quad \text{Equation (5)}$$

express the output volume velocity with $$U_o(x_o) = \frac{-S_{t2}}{\rho_0 c}(Ce^{-jkx_o} - De^{jkx_o}) \quad \text{Equation (6)}$$

wherein $\rho_0$ is the density of the air, $S_{t1}$ the cross-sectional area of the first impedance tube 11, $S_{t2}$ the cross-sectional area of the second impedance tube 12, $x_i$ the position of the input end 21, and $x_o$ the position of the output end 22. Then, substitute the first incident sound pressure A, the first reflected sound pressure B, the second incident sound pressure C and the second reflected sound pressure D into the corresponding Equations (3), (4), (5) and (6) to obtain the input sound pressure $p_i$, the input volume velocity Ui, the output sound pressure $p_o$ and the output volume velocity $U_o$.

In Step 5, express the acoustic impedance Z with $$Z = \begin{bmatrix} z_{11} & z_{12} \\ z_{21} & z_{22} \end{bmatrix}, \quad \text{Equation (7)}$$

undertaking measurements at the second outlet 122 in an opened condition and a closed condition, and using $$\begin{bmatrix} z_{11} & z_{12} \\ z_{21} & z_{22} \end{bmatrix} \begin{bmatrix} U_i \\ U_o \end{bmatrix} = \begin{bmatrix} p_i \\ p_o \end{bmatrix} \quad \text{Equation (8)}$$

to work out the acoustic impedance Z. In Step 5, Equation (8) can be further expressed as $$Zx = y. \quad \text{Equation (9)}$$

Let $Z = C_{yx}(C_{xx} + \epsilon I)^{-1}$, wherein $C_{yx} = yx^H$ and $C_{xx} = xx^H$, and wherein $C_{yx}$ is the cross-correlation matrix of y and x and $C_{xx}$ is the autocorrelation matrix of x, and wherein $\epsilon$ is a regularization coefficient and I is a unit matrix with a rank of 1. The unit matrix I is an ill-conditioned matrix. Therefore, undertake measurements of the second outlet 122 in an opened condition and a closed condition with a two-boundary method.

In the opened condition, let $Zx_1 = y_1$; in the closed condition let $Zx_2 = y_2$, whereby to obtain $$Z[x_1 x_2] = [y_1 y_2] \quad \text{Equation (10)}$$

Then, the acoustic impedance Z is acquired.

Alternatively, let $ZX = Y$, and let $z = C_{YX} C_{XX}^{-1}$, wherein $X = [x_1 x_2]$, $Y = [y_1 y_2]$, $C_{YX} = YX^H$, and $C_{xx} = XX^H$, wherein $C_{yx}$ is the cross-correlation matrix of y and x and $C_{xx}$ is the autocorrelation matrix of x. Then, use $$Z = C_{yx} C_{xx}^{-1} \quad \text{Equation (11)}$$

to acquire the acoustic impedance.

Figure 3A:
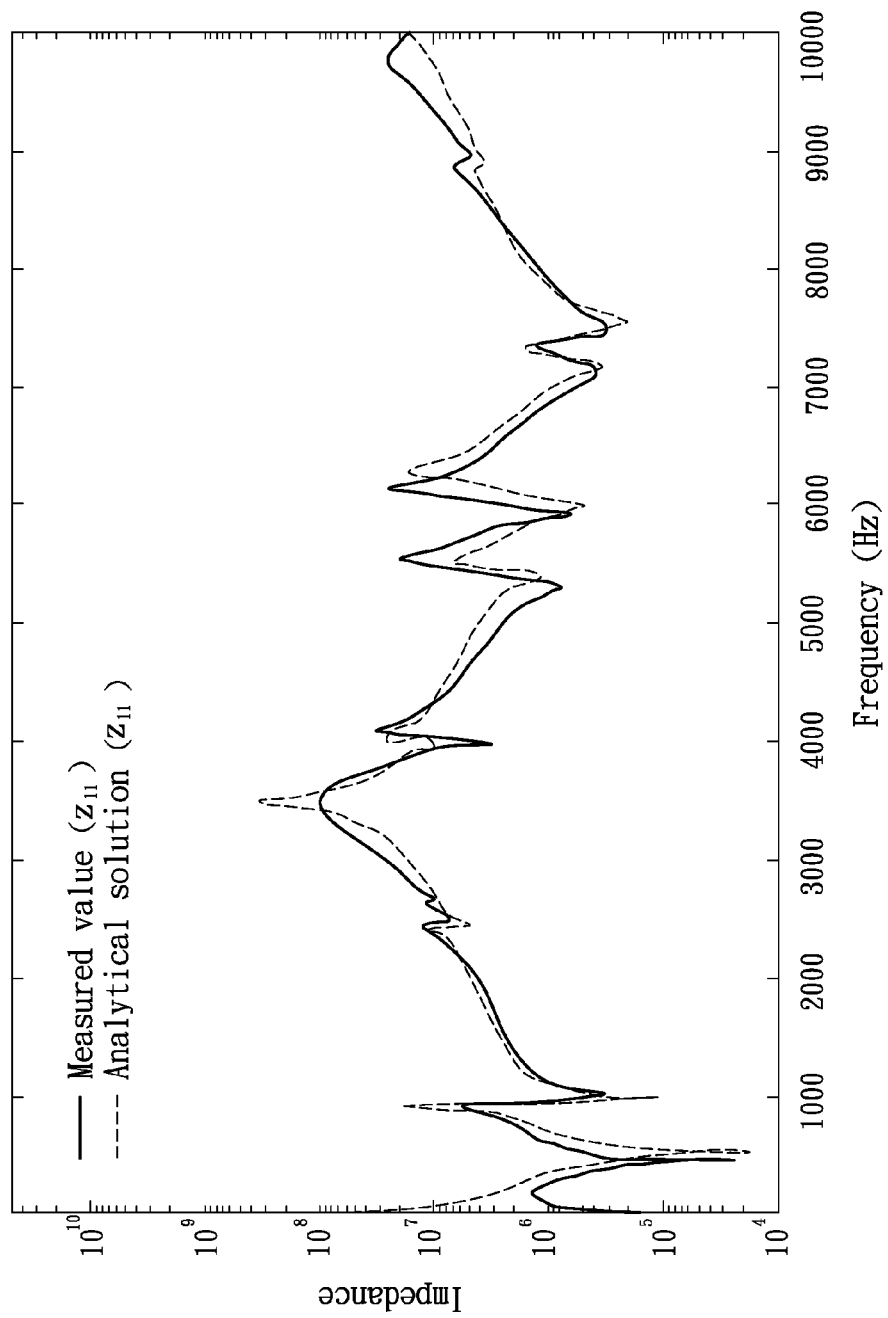
FIG. 3A shows the measured values and analytical solutions of $z_{11}$ of an asymmetric tested object according to one embodiment of the present invention.
Figure 3B:
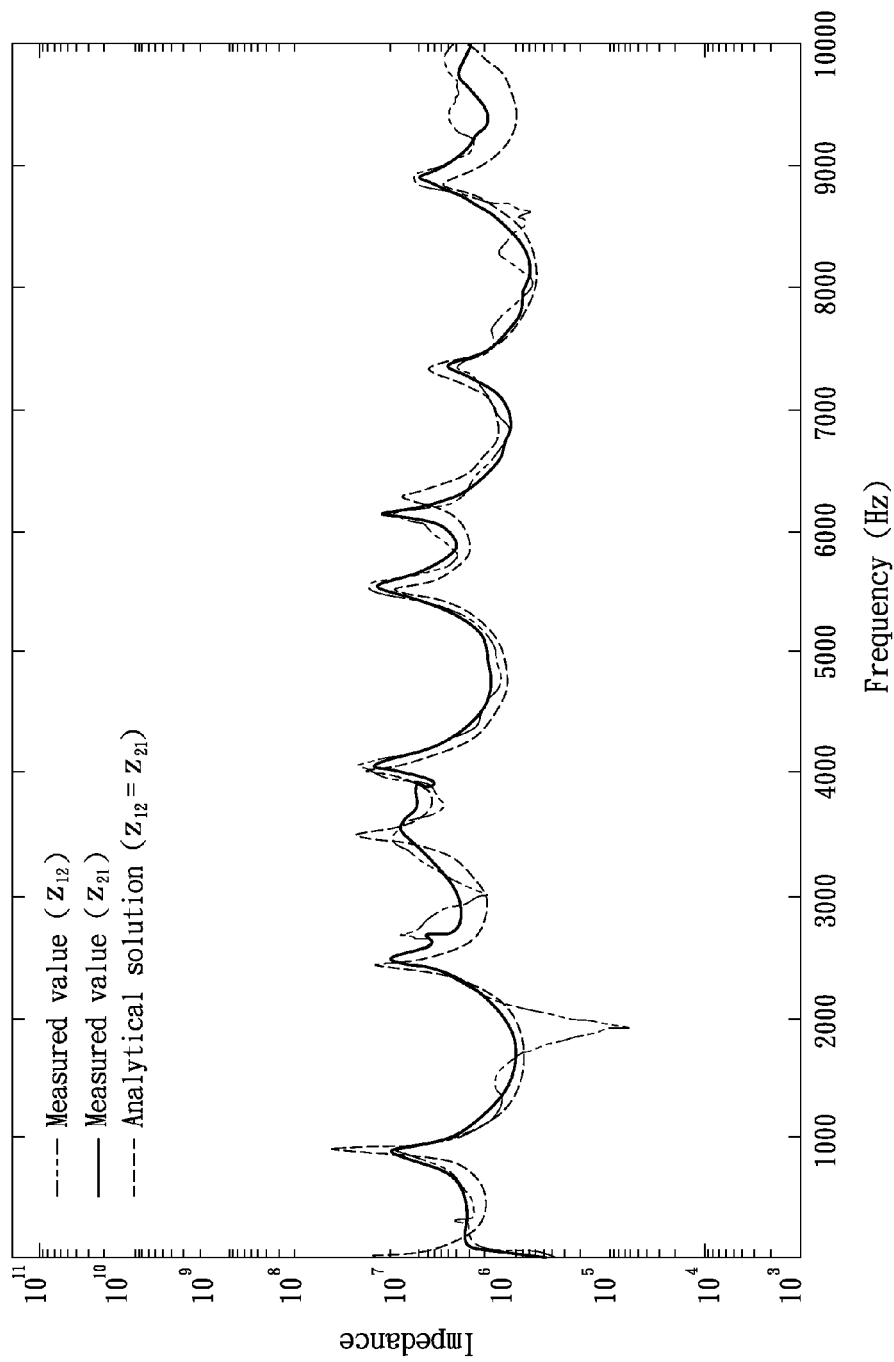
FIG. 3B shows the measured values and analytical solutions of $z_{12}$ and $z_{21}$ of an asymmetric tested object according to one embodiment of the present invention.
Figure 3C:
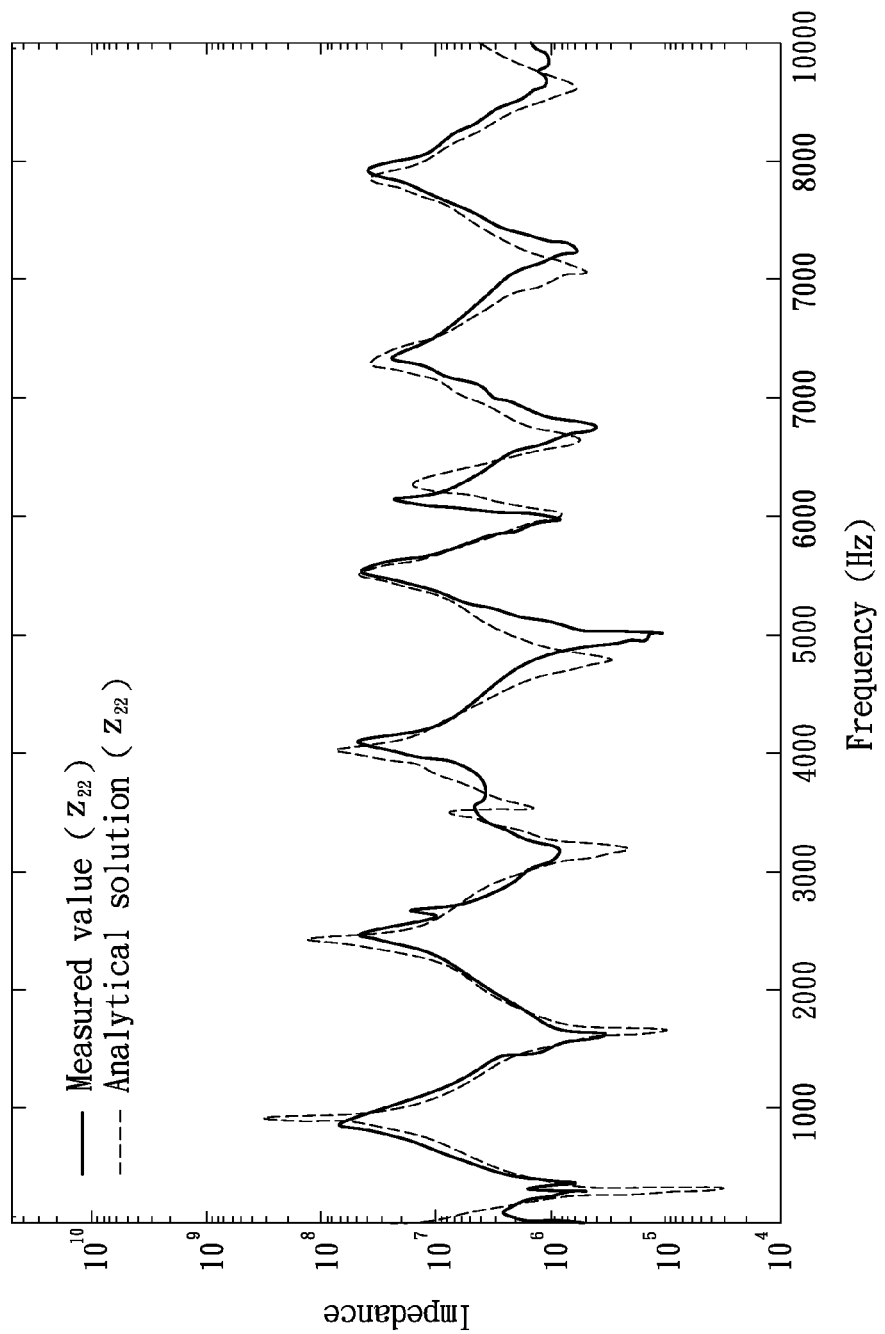
FIG. 3C shows the measured values and analytical solutions of $z_{22}$ of an asymmetric tested object according to one embodiment of the present invention.

Refer to FIGS. 3A-3C. FIG. 3A shows the measured values and analytical solutions of $z_{11}$ of an asymmetric tested object according to one embodiment of the present invention. FIG. 3B shows the measured values and analytical solutions of $z_{12}$ and $z_{21}$ of an asymmetric tested object according to one embodiment of the present invention. FIG. 3C shows the measured values and analytical solutions of $z_{22}$ of an asymmetric tested object according to one embodiment of the present invention. From FIGS. 3A-3C, it is learned: the measured values of the acoustic impedance Z (including $z_{11}$, $z_{12} = z_{21}$, and $z_{22}$) of an asymmetric tested object (such as the tested object 20b in FIG. 2B), which are acquired by the dual-port measurement system 10 with a two-boundary method, are very close to the analytical solutions. Therefore, the present invention has considerable accuracy and feasibility. It should be noted: the abovementioned example is only an exemplification, and the present invention does not limit that the tested object 20 must be an asymmetric tested object. In the present invention, the tested object 20 may also be a symmetric tested object 20a (as shown in FIG. 2A) or an asymmetric tested 20c with a sound source 23 (as shown in FIG. 2C).

Further, if the tested object 20 does not contain the sound source 23 but has a symmetric geometric shape (as shown in FIG. 2A) or an asymmetric geometric shape (as shown in FIG. 2B), the tested object 20 satisfies reciprocity. Thus, in Step 5, let $z_{12} = z_{21}$, and express Equation (8) as $$\begin{bmatrix} p_i \\ p_o \end{bmatrix} = \begin{bmatrix} z_{11} & z_{12} \\ z_{21} & z_{22} \end{bmatrix} \begin{bmatrix} U_i \\ -U_o \end{bmatrix}. \quad \text{Equation (8a)}$$

Next, use the two-boundary method to measure the second outlet 122 in an opened condition and a closed condition to obtain $$\begin{bmatrix} p_{i\_open} \\ p_{o\_open} \\ p_{i\_close} \\ p_{o\_close} \end{bmatrix} = \begin{bmatrix} U_{i\_open} & -U_{o\_open} & 0 \\ 0 & U_{i\_open} & -U_{o\_open} \\ U_{i\_close} & -U_{o\_close} & 0 \\ 0 & U_{i\_close} & -U_{o\_close} \end{bmatrix} \begin{bmatrix} z_{11} \\ z_{12} \\ z_{22} \end{bmatrix}. \quad \text{Equation (8b)}$$

Then, use a least square method to solve Equation (8b) to obtain $z_{11}$, $z_{12}$ and $z_{22}$ and acquire the acoustic impedance Z.

Figure 4A:
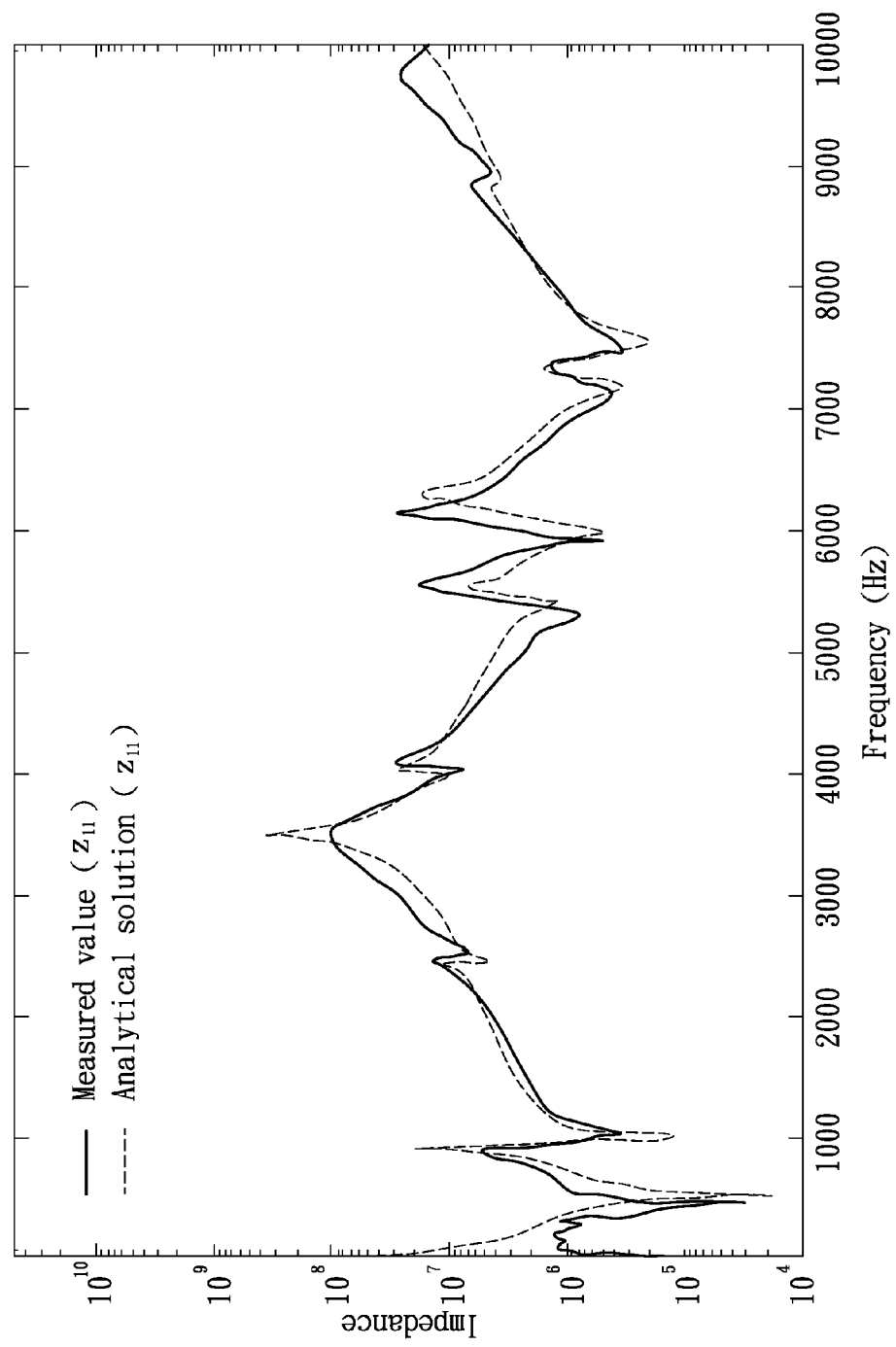
FIG. 4A shows the measured values and analytical solutions of $z_{ii}$ of an asymmetric tested object according to another embodiment of the present invention.
Figure 4B:
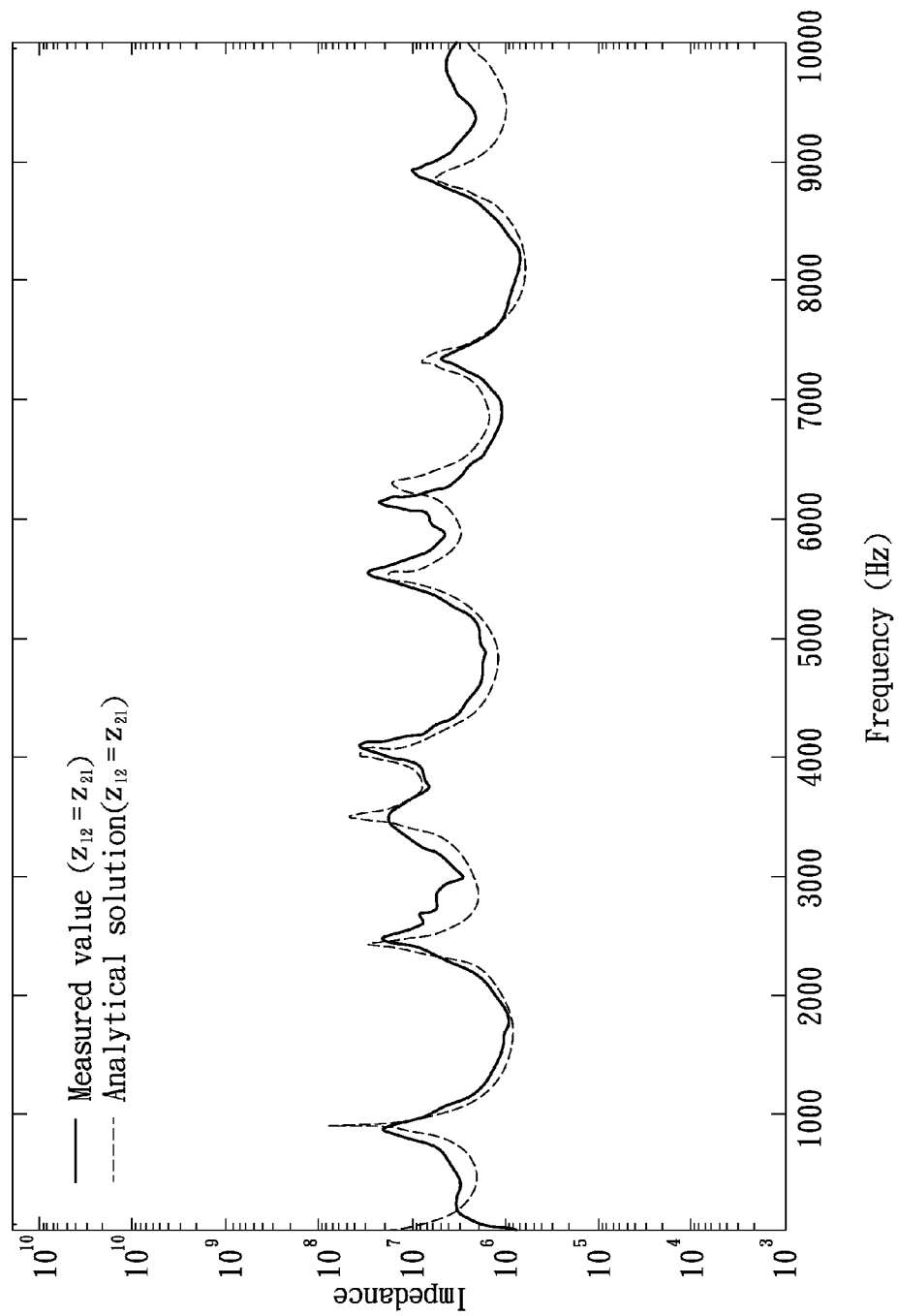
FIG. 4B shows the measured values and analytical solutions of $z_{12}$ and $z_{21}$ of an asymmetric tested object according to another embodiment of the present invention.
Figure 4C:
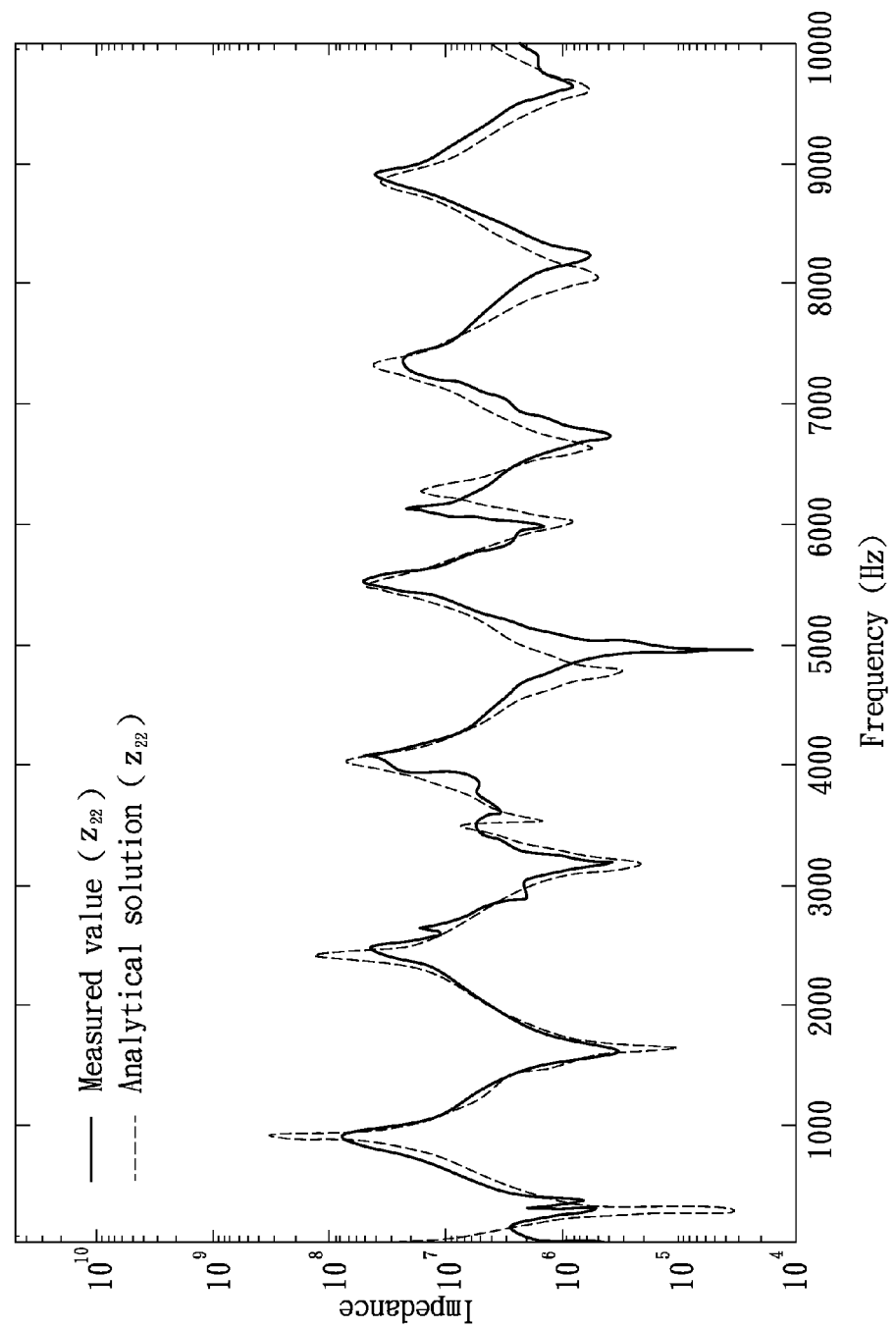
FIG. 4C shows the measured values and analytical solutions of $z_{22}$ of an asymmetric tested object according to another embodiment of the present invention.

In one embodiment, the present invention uses the least square method to obtain the acoustic impedance Z (including $z_{11}$, $z_{12}=z_{21}$, and $z_{22}$) of an asymmetric tested object satisfying reciprocity, such as the tested object 20*b* shown in FIG. 2B. Refer to FIGS. 4A-4C for the measured values and the analytical solutions of $z_{11}$, $z_{12}=z_{21}$, and $z_{22}$. From FIGS. 4A-4C, it is learned: the measured values of the acoustic impedance Z (including $z_{11}$, $z_{12}=z_{21}$, and $z_{22}$) of an asymmetric tested object satisfying reciprocity, which are acquired by the dual-port measurement system 10 and the least square method, are very close to the analytical solutions. Therefore, the present invention also has considerable accuracy and feasibility in using the least square method to obtain acoustic impedance of a tested object satisfying reciprocity.

In conclusion, the present invention uses the dual-port measurement system, which is adaptive to various types of tested objects, to obtain the acoustic impedances Z of the tested objects. The present invention is conveniently applied to various fields, such as the design of earphones, muffler tubes, sound absorption materials, and artificial ears. Further, the present invention provides different methods for different types of tested objects to solve the acoustic impedance Equations. Therefore, the present invention possesses utility, novelty and non-obviousness and meets the condition for a patent. Thus, the Inventors file the application for a patent. It is appreciated if the patent is approved fast.

The present invention has been demonstrated in detail with the embodiments described above. However, these embodiments are only to exemplify the present invention but not to limit the scopes of the present invention. Any equivalent modification or variation according to the spirit of the present invention is to be also included within the scope of the present invention.

What is claimed is:

1. A method of using a dual-port measurement system to measure acoustic impedance, which is used to measure an acoustic impedance Z of a tested object, wherein the tested object includes an input end and an output end opposite to the input end, and wherein the dual-port measurement system comprises a first impedance tube and a second impedance tube, and wherein the first impedance tube includes a first inlet where a plane wave of a sound source is input, and a first outlet connected with the input end, and wherein the second impedance tube includes a second inlet connected with the output end, and a second outlet where the plane wave is output, wherein the method comprises:

Step 1: arranging a plurality of microphones inside the first impedance tube and the second impedance tube respectively and lengthwise;

Step 2: expressing sound pressures measured by the microphones inside the first impedance tube with $$p_M = Ae^{-jkx_M} + Be^{jkx_M}, \text{ and} \quad \text{Equation (1)}$$

expressing sound pressures measured by the microphones inside the second impedance tube with $$p_M = Ce^{-jkx_M} + De^{jkx_M}, \quad \text{Equation (2)}$$

wherein $p_M$ is a sound pressure measured by an Mth microphone, $x_M$ a position of the Mth microphone, A a first incident sound pressure, B a first reflected sound pressure, C a second incident sound pressure, D a second reflected sound pressure, and k a wave number;

Step 3, using Equations (1) and (2) and practical sound pressures measured by the microphones to work out A, B, C and D;

Step 4: expressing an input sound pressure of the input end with $$p_i(x_i) = Ae^{-jkx_i} + Be^{jkx_i}, \quad \text{Equation (3)}$$

expressing an input volume velocity of the input end with $$U_i(x_i) = \frac{S_{t1}}{\rho_0 c}(Ae^{-jkx_i} - Be^{jkx_i}), \quad \text{Equation (4)}$$

expressing an output sound pressure of the output end with $$p_o(x_o) = Ce^{-jkx_o} + De^{jkx_o}, \text{ and} \quad \text{Equation (5)}$$

expressing an output volume velocity of the output end with $$U_o(x_o) = \frac{-S_{t2}}{\rho_0 c}(Ce^{-jkx_o} - De^{jkx_o}), \quad \text{Equation (6)}$$

wherein $\rho_0$ is a density of air, $S_{t1}$ a cross-sectional area of the first impedance tube, $S_{t2}$ a cross-sectional area of the second impedance tube, $x_i$ a position of the input end, and $x_o$ a position of the output end;

Step 5: expressing the acoustic impedance Z with $$Z = \begin{bmatrix} z_{11} & z_{12} \\ z_{21} & z_{22} \end{bmatrix}, \quad \text{Equation (7)}$$

undertaking measurements at the second outlet in an opened condition and a closed condition, and using $$\begin{bmatrix} z_{11} & z_{12} \\ z_{21} & z_{22} \end{bmatrix} \begin{bmatrix} U_i \\ U_o \end{bmatrix} = \begin{bmatrix} p_i \\ p_o \end{bmatrix} \quad \text{Equation (8)}$$

to work out the acoustic impedance Z.

2. The method of using a dual-port measurement system to measure acoustic impedance according to claim 1, wherein the tested object includes a sound source.

3. The method of using a dual-port measurement system to measure acoustic impedance according to claim 1, wherein in Step 5, Equation (8) is further expressed as $$Zx = y, \text{ whereby } Z = C_{yx}(C_{xx} + \epsilon I)^{-1}, \quad \text{Equation (9)}$$

wherein $C_{yx}$ is a cross-correlation matrix of y and x, $C_{xx}$ an autocorrelation matrix of X, $\epsilon$ a regularization coefficient, and I a unit matrix.

4. The method of using a dual-port measurement system to measure acoustic impedance according to claim 1, wherein the input end and the output end of the tested object are symmetric.

5. The method of using a dual-port measurement system to measure acoustic impedance according to claim 1, wherein the input end and the output end of the tested object are asymmetric.

6. The method of using a dual-port measurement system to measure acoustic impedance according to claim 1, wherein in Step 5, the tested object satisfies reciprocity; let $z_{12}=z_{21}$, and Equation (8) is further expressed as $$\begin{bmatrix} p_i \\ p_o \end{bmatrix} = \begin{bmatrix} z_{11} & z_{12} \\ z_{21} & z_{22} \end{bmatrix} \begin{bmatrix} U_i \\ -U_o \end{bmatrix}, \qquad \text{Equation (8a)}$$

and wherein a least square method is used to solve $z_n$, $z_{12}$ and $z_{22}$ and acquire the acoustic impedance Z.

* * * * *